United States Patent [19]
Suitor et al.

[11] Patent Number: 4,885,142
[45] Date of Patent: Dec. 5, 1989

[54] APPARATUS IN THE FORM OF A DISK FOR THE SEPARATION OF OXYGEN FROM OTHER GASES AND/OR FOR THE PUMPING OF OXYGEN AND THE METHOD OF REMOVING THE OXYGEN

[75] Inventors: Jerry W. Suitor, El Toro; C. Martin Berdahl, Sierra Madre; Wilbur J. Marner, Arcadia, all of Calif.

[73] Assignee: California Institute of Technology, Pasadena, Calif.

[21] Appl. No.: 923,160

[22] Filed: Oct. 24, 1986

Related U.S. Application Data

[63] Continuation-in-part of Ser. No. 791,709, Oct. 28, 1985, abandoned.

[51] Int. Cl.$^4$ .............................................. C01B 13/00
[52] U.S. Cl. .................................... 423/219; 423/579; 204/255; 204/256; 204/257; 204/258; 204/263; 204/265; 204/266; 204/267; 204/268; 204/270; 204/275; 204/277; 204/278; 204/284; 204/301

[58] Field of Search ................................. 423/219, 579; 204/299 R, 301, 129, 270, 212, 255–258, 263–266, 275, 277, 278, 284

[56] References Cited

U.S. PATENT DOCUMENTS 4,056,452 11/1977 Campbell .......................... 204/258
4,528,078 7/1985 Hirschfeld .......................... 204/129

Primary Examiner—John F. Niebling
Assistant Examiner—Kathryn Gorgos
Attorney, Agent, or Firm—Paul R. Wylie

[57] ABSTRACT

An apparatus in the form of a disk for the separation of oxygen from gases, or for the pumping of oxygen, uses a substantially circular disk geometry for the solid electrolyte with radial flow of gas from the outside edge of the disk to the center of the disk. The reduction in available surface area as the gas flows toward the center of the disk reduces the oxygen removal area proportionally to provide for a more uniform removal of oxygen.

15 Claims, 3 Drawing Sheets ated May 22, 1987.

APPARATUS IN THE FORM OF A DISK FOR THE SEPARATION OF OXYGEN FROM OTHER GASES AND/OR FOR THE PUMPING OF OXYGEN AND THE METHOD OF REMOVING THE OXYGEN

ORIGIN OF THE INVENTION

The invention described herein was made in the performance of work under a NASA contract and is subject to the provisions of Section 305 of the National Aeronautics and Space Act of 1958, Public Law 85.568 (72 Stat 435; 42 USC 2457).

This application is a Continuation-in-Part of application Ser. No. 791,709 filed Oct. 28, 1985 now abandoned May 22, 1987.

BACKGROUND OF THE INVENTION

Many, solid oxides, such as stabilized zirconia, behave like semi-conductors except that instead of conducting electrons, they conduct oxygen ions. Previously used tubular and flat plate cell geometry arrangements for removing oxygen from oxygen-containing gas, or for pumping substantially pure oxygen streams, have had very uneven oxygen removal distributions or oxygen pumping efficiencies, due to electrical current mal-distribution over the cell. This has resulted in excessive solid electrolyte requirements and excessive power consumption. Moreover, there, has been a tendency to damage the solid electrolyte due to over depletion of the oxygen-containing gas stream.

SUMMARY OF THE INVENTION

According to this invention, the solution to the foregoing problem lies in the use of substantially circular disk geometry for the solid electrolyte with radial flow of feedstock gas from the outside edge of the disk to the center. The reduction in available surface area as the gas flows toward the center of the disk reduces the oxygen removal proportionally to provide for a more uniform removal of oxygen through the disk.

The uniqueness of the circular disk design is in the radial feedstock gas flow inward toward the center of the disk. As the gas flows towards the disk center, oxygen is removed. The lower oxygen partial pressure causes an increase in the Nernst bucking voltage. With linear flow configurations such as a tube or square plate, the oxygen partial pressure drops quickly producing a high Nernst bucking voltage and, therefore, a high power consumption. The radial flow of the circular disk subjects the gas to a reduced active area as the flow moves toward the center. Therefore, the oxygen removal rate is reduced, and the partial pressure of oxygen does not drop as dramatically as with linear flow arrangements.

According to one form of the invention there is provided an apparatus for the separation and/or pumping of oxygen from a feedstock containing oxygen, as defined herein which includes a disk of oxygen conductive solid electrolyte adapted to be contacted with electrode means to produce a flow of oxygen ions therethrough. Means are provided to flow the feedstock radially inwardly from the circumference of the disk.

According to the method aspect of the invention a disk of oxygen conductive solid electrolyte material is provided. A feedstock containing oxygen is supplied to a peripheral portion of the disk, and said feedstock is passed radially inwardly over the input surface of the disk. A current is applied to the disk in a manner such that oxygen is removed from said feedstock through said disk.

The term "feedstock containing oxygen" includes those feedstocks which include oxygen as a component, such as air and gaseous oxides, as well as substantially pure oxygen feedstocks. In the latter case, the inventive apparatus and method serves to pump oxygen.

It is an object of this invention to provide an apparatus for separating oxygen from a feedstock containing oxygen. It is a further object of this invention to provide a method and apparatus to pump oxygen.

Another object of this invention is the provision of a method and apparatus to obtain oxygen from air.

A still further object of this invention is the provision of a method and apparatus of the foregoing type that can be operated efficiently and economically.

Another object of this invention is the provision of an apparatus of the foregoing type which can be constructed easily and operated reliably.

In attempting to provide an apparatus for the separation of oxygen and other gases, and for the pumping of oxygen, the various objects of the invention were met by providing an apparatus as previously described wherein the prior art problems in utilizing a solid electrolyte were overcome to attain a unit operating at increased efficiency.

DESCRIPTION OF THE DRAWINGS

The invention will be more fully understood with reference to the following drawings wherein.

Figure 1:
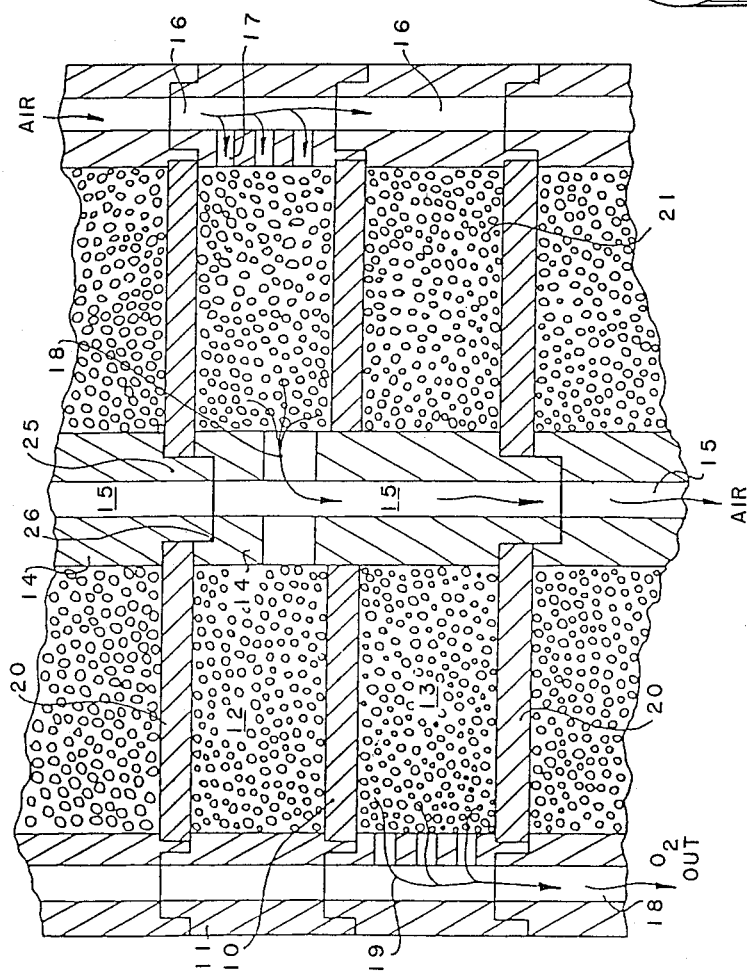
FIG. 1 represents a cross-sectional elevation of one embodiment of the apparatus according to this invention.

Referring now to the drawings, and particularly to FIG. 1, there is shown therein a disk 10 of solid electrolyte that is adapted to be contacted with electrode means (to be hereinafter described) to produce a flow of oxygen ions therethrough. Gas impervious side wall members 11 extend circumferentially around both sides of disk 10 to define an input chamber 12 and an output chamber 13 on opposite sides thereof. A central core member 14 is provided having an output passage 15 therein with said core member 14 extending axially on both sides of said disk 10. Side wall member 11 includes at least one feedstock passage 16 being in fluid communication with inlet chamber 12 through ports 17. Side wall member 11 further includes at least one oxygen outlet passage 18 in fluid communication with outlet chamber 13 via ports 19. Second disk means 20 are provided opposite disk 10 to provide end walls for the input chamber 12 and the output chamber 13. Such second disk means 20 are of an electronically conducting gas impervious material.

Input and output chambers 12 and 13 respectively, can be filled with a porous packing material 21 which is electronically conductive to serve as an electrode means for disk 10. The material 21 is a porous or powdered ceramic material which can be fabricated from a conductive rare earth oxides, and it can also be a sintered material. In a preferred form of the invention such rare earth oxide is selected from the group consisting of perovskites, pseudo perovskites and spinels. In a still further preferred form of the invention such rare earth oxide is a lanthanum-strontium-manganese oxide.

Figure 2:
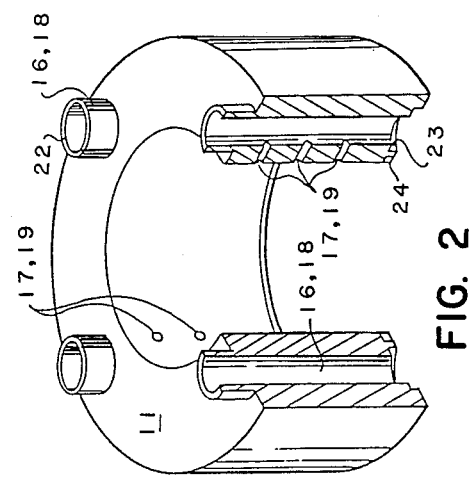
FIG. 2 represents a view in perspective of one of the members of the apparatus shown in FIG. 1.

As best shown in FIG. 2, the side wall members 11 are formed as a solid gas impervious ring, with feedstock passage 16 and oxygen outlet passage 18 formed as circular passages therethrough with outlet ports 17 serving to permit the entry of feedstock into input chamber 12. Offset 90 degrees in the embodiment shown are outlet passages 18, which, in the unit illustrated in FIG. 2, do not have fluid communication ports. It will be apparent to one skilled in the art, that side wall member 10 can be used as a side wall for both input and output chambers 12 and 13 by simply rotating the unit 90 degrees when it is used as a side wall for an outlet chamber. Thus, the ports 17 will serve as input ports for inlet chamber 12 and for outlet ports 19 when the unit is rotated 90 degrees for output chamber 13. While the configuration shown utilizes two ports 17 and 19 for each chamber, more passages and ports can be utilized to obtain desired distribution.

Extensions 22 of sidewall member 11 are adapted to interfit with recess 23 of the next adjoining such sidewall member in interfitting substantially sealing relationship. Internal groove 24 is also provided to interfit with second disk 20, again in substantially gas sealing relationship.

Core member 14 is provided with extension 25 which is adapted to mate with recess 26 in next adjoining core member 14. In a preferred form of the invention, core member 14 and disk 10 are formed as an integral unit.

As shown in FIG. 1, a number of the disk, sidewall member and core units can be assembled in a manner such that they will be connected for communication with incoming feedstock in parallel and electrically connected in series by means of the electrically conductive porous packing material 21 and second disk means 20.

Figure 3:
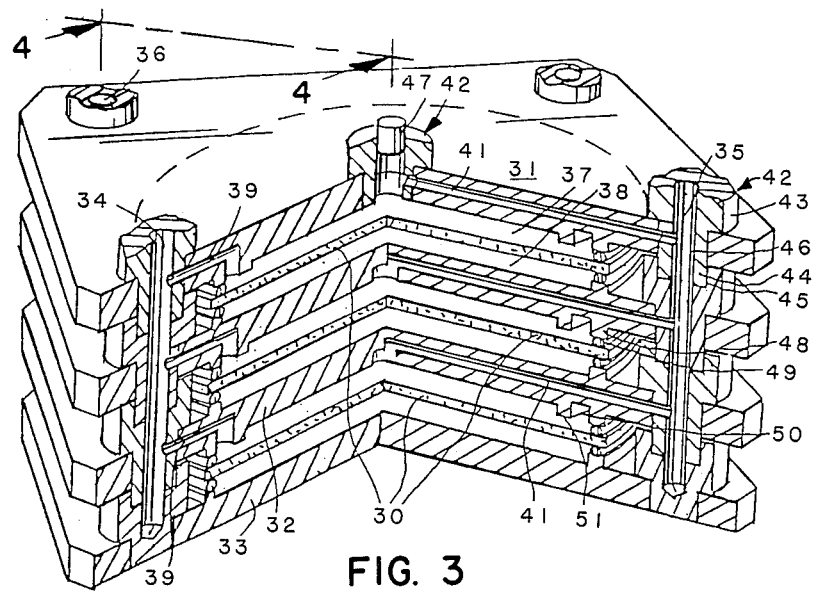
FIG. 3 is a view in perspective showing an alternate embodiment of the apparatus of the invention, with parts thereof broken away for illustration purposes.
Figure 4:
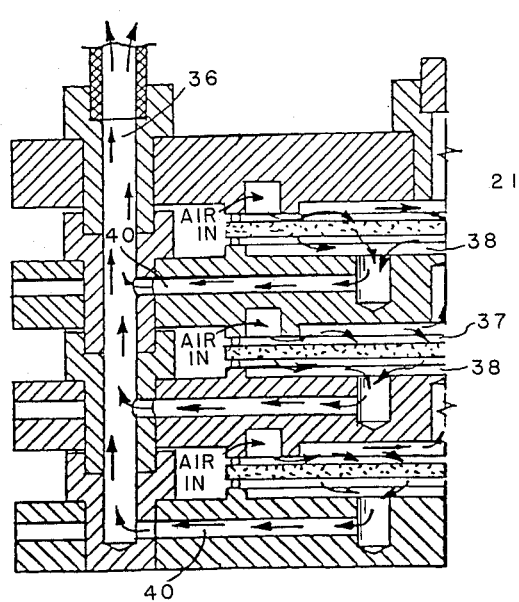
FIG. 4 is a sectional view taken on line 4—4 of FIG. 3 looking in the direction of the arrows.

In an alternate preferred embodiment according to the invention as shown in FIG. 3 and FIG. 4, a plurality of disks of oxygen conductive solid electrolyte material 30 are shown in an arrangement where individual cells including such disks are in a stack arrangement. In FIG. 3, there are shown four disks 30 in the stack, however more disks could be utilized.

The arrangement in FIG. 3 includes a gas impervious top plate 31, intermediate plates 32 and a bottom plate 33. The plates are interfitted and stacked together in a manner to form air inlets 34, oxygen depleted air outlet 35, and oxygen outlet 36. Formed on the respective sides of disks 30 are input chamber 37 and output chamber 38. Input chamber 37 communicates through inlet conduit 39 which is in fluid communication with feedstock passage 34. Output chamber 38 communicates through outlet conduit 40 (shown in FIG. 4) which is in fluid communication with output passage 36. Inlet chamber 37 is also in fluid communication with second outlet conduit 41 which is in fluid communication with oxygen depleted air outlet passage 35.

The passages 34, 35 and 36 are formed by manifold bushings 42 which are formed with flanges 43 and interfitting male and female connecting portions 44 and 45 respectively and internal bores 46 to form the respective passages. Intermediate plates 32 are provided with inlet conduits 39, outlet conduits 40 and second outlet conduits 41, whereas top plate 31 is provided only with second outlet conduit 41 and bottom plate 33 is provided only with outlet conduit 40. In addition, top plate 31 is provided with a manifold bushing 42 for the purposes of installing a thermocouple chimney which is closed to gas flow by means of plug 47 or other suitable means.

Input chamber 37 and output chamber 38 are of essentially circular cross-section being bounded by peripheral rings 48.

Circular disks 30 are mounted between the respective plates 31, 32 and 33 by means of platinum wire contact rings 49 which provide the electrical connection to the disks 30.

Inlet conduit 39 connects to circumferential plenum 50 which distributes the inlet feedstock around the periphery of inlet chamber 37 at a location substantially on the outer circumference of disk 30. Feedstock bleeds from the plenum 50 under ring 51 to enter input chamber 37.

It is preferred that the disks 10 and 30 be of circular configuration to achieve a more uniform oxygen removal by providing radial flow of gas from the outside edge of the disk towards its center. Thus, as air or oxygen enters inlet chamber 12 or 37 the gas proceeds radially toward the center of disk 10 or 30. The reduction in available surface area over disk 10 or 30 as the gas moves inwardly reduces the oxygen removal proportionally to provide for a more uniform removal of the oxygen from the feedstock. Substantially pure oxygen passing through disk 10 or 30 by electrodialysis flows through the apparatus to oxygen outlet passage 18 or 36 respectively.

Figure 6:
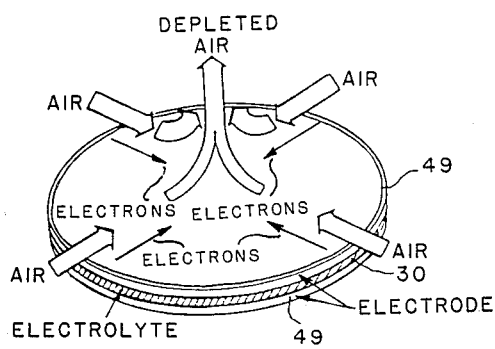
FIG. 6 is a view similar to FIG. 5 showing the radial current operation of the apparatus of FIG. 3.
Figure 5:
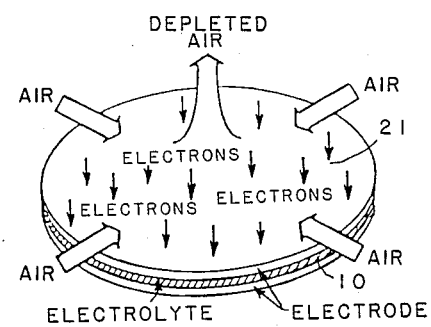
FIG. 5 is a schematic view showing the axial current operation of the apparatus of FIG. 1.

FIGS. 5 and 6 illustrate the mode of operation of the apparatus of FIGS. 1 and 3 respectively. FIG. 5 shows the axial current operation of the apparatus in FIG. 1 wherein the porous packing material electrode 21 distributes the electrons across the surface of disk 10 where they are directed through the disk in an axial direction. In FIG. 6, the current is distributed circumferentially around the edge of disk 30 by platinum wire contact rings 49, serving as electrodes, and electrons are directed radially inwardly within disk 30.

Figure 7:
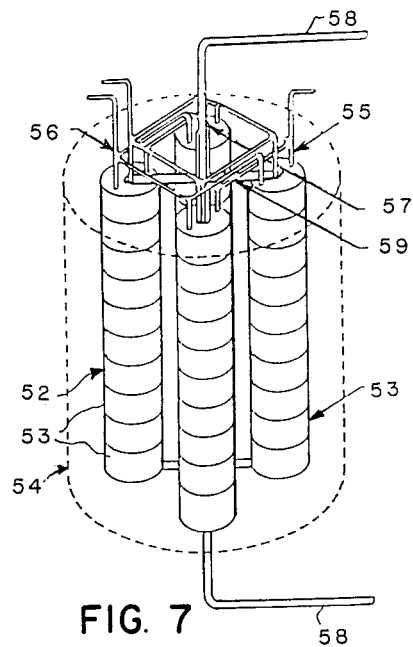
FIG. 7 is a schematic view showing an arrangement of four separate stacks of individual cells of the apparatus according to the invention.

In FIG. 7, there is shown a plurality of stacks 52 of individual cells 53. Each cell comprises a solid electrolyte disk 10 or 30 and the other components as described above to form the necessary input chambers and output chambers. As shown in FIG. 7, the four stacks 52 and related hardware comprise a module 54. The stacks 52 are supplied with air through supply air manifold 55 which connects with feed stock passage 16 if the cells 53 are of the configuration shown in FIGS. 1 and 2, or alternatively, feed stock passage 34 if the cells are of the configuration shown in FIGS. 3 and 4. Oxygen manifold 56 is similarly connected to oxygen outlet passage 18, as shown in FIGS. 1 and 2 or oxygen outlet passage 36 as shown in FIGS. 3 and 4. Oxygen depleted air manifold 57 communicates with output passage 15 in the case of the cells of FIGS. 1 and 2, or oxygen depleted air outlet 35 in the case of the cells of FIGS. 3 and 4. Electrical power is supplied to the module by electrical conduits 58. The power is distributed to each stack 51 by means of a busbar 59.

Figure 8:
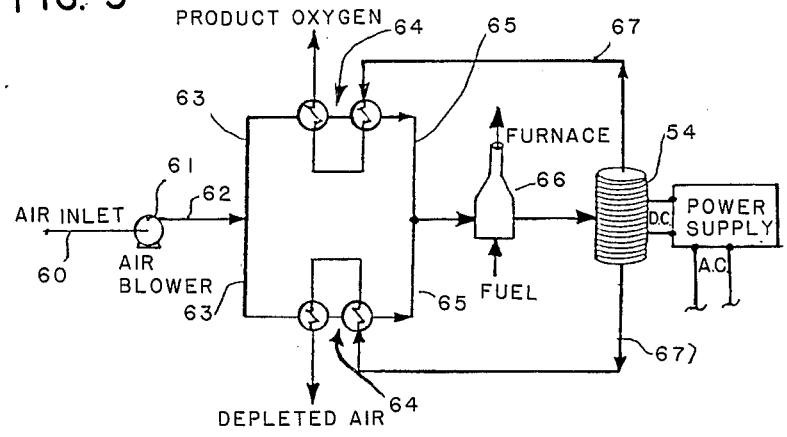
FIG. 8 is a schematic view showing the layout of a system for producing oxygen using the apparatus according to the invention; and, FIG. 9 is a schematic view showing a preferred electrical connection for the inventive apparatus.

In FIG. 8, there is shown the layout for a system for producing oxygen from air using the module 54 of FIG. 7. The system includes air inlet 60, air blower 61 and conduit 62 which divides into conduits 63 to deliver the air to heat exchanger trains 64. In the heat exchangers 64, the air is preheated, extracting energy contained in gases exhausting from module 54. The air streams then pass through conduits 65 and are recombined and pass through furnace 66 which adds additional heat to permit operation at the desired elevated temperature. In module 54 itself, additional heat recovery will be made to absorb heat generated by ohmic heating in the module. After separation in the module, the oxygen depleted air and the oxygen flow by means of conduits 67 to heat exchanger train 64.

Figure 9:
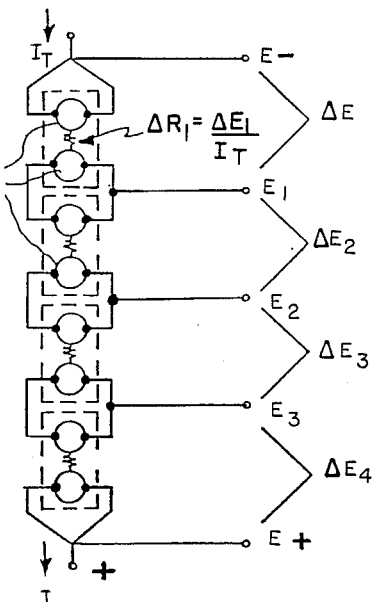

Referring now to FIG. 9, there is shown schematically electrical connection for the inventive apparatus wherein power is supplied to either platinum wire contact rings 49 or to porous electrode material 21. In the arrangement shown, the cells 53 of a stack 52 are shown connected in series to result in identical current through each cell.

The invention may be embodied in other specific forms without departing from the spirit or essential characteristics thereof. The present embodiments are therefore to be considered in all respects as illustrative and not restrictive, the scope of the invention being indicated by the appended claims; and all changes which come within the meaning and range of equivalency of the claims are therefore intended to be embraced therein.

What is claimed is:

1. An apparatus for the separation or pumping of oxygen from a feedstock containing oxygen or oxygen comprising:
   a. a disk of oxygen conductive solid electrolyte positioned such that an input side thereof is adapted to be in fluid contact with a feedstock containing oxygen and an output side thereof is in contact with an oxygen removal means, said disk being adapted to be contacted with electrodes to produce a flow of oxygen ions there through;
   b. means to supply said feed stock containing oxygen to a peripheral portion of the input side of said disk; and,
   c. means to provide flow of said feedstock containing oxygen radially inwardly from points around the peripheral portion of said disk to a center portion thereof.

2. An apparatus according to claim 1 further comprising oxygen depleted feedstock removal means located adjacent the input side of said solid electrolyte.

3. An apparatus according to claim 1 further comprising an oxygen removal means located adjacent the output side of said solid electrolyte.

4. An apparatus according to claim 1 comprising input and output chambers formed on the input and output sides of said disk.

5. An apparatus according to claim 4 wherein said input and output chambers are formed with said disk and by top and bottom plate means respectively.

6. An apparatus according to claim 5 wherein conduit means are incorporated in said top plate means to supply said feedstock to a peripheral section of the input side of said disk of solid electrolyte.

7. An apparatus according to claim 5 wherein said conduit means comprises a circumferential plenum located adjacent the periphery of said disk of solid electrolyte, said plenum being in fluid communication with said input chamber.

8. An apparatus according to claim 5 comprising a plurality of said disks of solid electrolyte arranged to form a stack of cells.

9. An apparatus according to claim 8 wherein at least one of said cells other than the top and bottom cells of said stack has said top and bottom plate means defined by a single gas impervious plate said single gas impervious plate defining a top plate means for a cell in the stack and said plate also defining a bottom plate means for the next adjacent higher cell in the stack.

10. An apparatus according to claim 1 wherein said disk is circular.

11. An apparatus according to claim 1 further comprising electrode means positioned to contact said disk at the periphery thereof.

12. An apparatus according to claim 2 further comprising electrode means in the form of an electronically conductive porous material spread over the input side of said disk.

13. A method of removing oxygen from a feedstock containing oxygen comprising:
   a. providing a disk of oxygen conductive solid electrolyte material;
   b. contacting a peripheral portion of said disk with a feedstock containing oxygen in a manner such that said feedstock moves radially inwardly from points around the periphery toward the center of said disk; and,
   c. applying a current to said disk in a manner such that oxygen is removed from said feedstock containing oxygen through said disk to an output side thereof.

14. A method according to claim 13 wherein said current is applied to the periphery of said disk whereby electrons are directed radially inwardly within said disk.

15. A method according to claim 14 wherein said current is applied across the input surface of said disk whereby electrons are directed axially within said disk.

* * * * *